United States Patent
Mitschke et al.

(10) Patent No.: US 6,673,955 B2
(45) Date of Patent: Jan. 6, 2004

(54) PREPARATION OF TRIETHYL PHOSPHATE

(75) Inventors: Karl-Heinz Mitschke, Odenthal (DE); Kaspar Hallenberger, Leverkusen (DE); Ottfried Schlak, Überlingen (DE); Johannes Kaulen, Odenthal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/302,543

(22) Filed: Nov. 22, 2002

(65) Prior Publication Data

US 2003/0100788 A1 May 29, 2003

(30) Foreign Application Priority Data

Nov. 27, 2001 (DE) ......................................... 101 58 135

(51) Int. Cl.$^7$ .................................................. C07F 9/02
(52) U.S. Cl. .......................... 558/92; 558/95; 987/223; 987/232
(58) Field of Search ...................... 558/92, 95; 987/223, 987/232

(56) References Cited

U.S. PATENT DOCUMENTS 6,034,260 A * 3/2000 Mitschke et al. ............. 558/92

FOREIGN PATENT DOCUMENTS

| DE | 541 145 | 1/1932 |
| DE | 899 498 | 6/1954 |
| KR | 9501703 | 2/1995 |

* cited by examiner

Primary Examiner—Joseph K. McKane
Assistant Examiner—Ebenezer Sackey
(74) Attorney, Agent, or Firm—Godfried R. Akorli; Diderico van Eyl

(57) ABSTRACT

The invention relates to a process for preparing triethyl phosphate by reacting phosphorus oxychloride with a greater than stoichiometric quantity of ethanol under reduced pressure at temperatures of from 0 to 50° C. in a reaction vessel, wherein a) the volatile components resulting from the reaction are predominantly condensed by means of a reflux condenser and the remaining volatile components are passed into a scrubber filled with water, b) after the end of the reaction, the reaction mixture is separated distillatively in an outgassing column into a top product and a bottom product which predominantly comprises triethyl phosphate, c) the top product of the outgassing column is combined with the contents of the scrubber and d) the contents of the scrubber are separated distillatively in an azeotropic distillation to obtain water and ethanol as top product and the ethanol, preferably after dewatering, is preferably returned to the reaction.

15 Claims, No Drawings

PREPARATION OF TRIETHYL PHOSPHATE

BACKGROUND OF THE INVENTION

1. Field of the Invention

The invention relates to a process for preparing triethyl phosphate by reacting phosphorus oxychloride with ethanol.

2. Brief Description of the Prior Art

Trialkyl phosphates have a broad application spectrum. They serve, for example, as plasticizers, unreactive flame retardants, hardeners and accelerants in plastics and coatings, and are used as auxiliaries in textiles and paper. They also find use in the chemical industry as wetting agents, flotation agents, defoamers, emulsifiers, stabilizers or as extractants.

A variety of processes for preparing trialkyl phosphates from phosphorus oxychloride and the corresponding alcohols are known. In the past, attempts were made to improve the process with regard to the reaction temperature, ratio of the components used and removal of the heat of reaction. A problem in the reaction of these two components is that hydrogen chloride, which is formed has to be removed from the reaction mixture very quickly and completely, in order to avoid acidolytic cleavage of the esters formed.

DE 541 145 C describes a process for preparing phosphate esters of aliphatic alcohols which react phosphorus oxychloride with the corresponding alcohols at reduced pressure and elevated temperature, so that hydrogen chloride is continually removed from the reaction mixture. A disadvantage of the application of this process for preparing triethyl phosphate is that it leads to considerable losses of ethanol, which is likewise removed from the reaction mixture under the reaction conditions.

DE 899 498 C and U.S. Pat. No. 2,636,048 disclose the removal of hydrogen chloride from the reaction mixture by passing in inert gas. This measure likewise leads disadvantageously to considerable losses of ethanol when preparing triethyl phosphate.

The abstract of KR 9501703 A discloses the use of both solvents which only dissolve hydrogen chloride to a small extent and also of bases which neutralize hydrogen chloride in the reaction mixture. A disadvantage thereof is that the use of solvents is associated with a reduced space-time yield. Although the use of bases avoids acidolytic cleavage of the reaction products, neutralization of the reaction mixture, in addition to the costs of the neutralizing agent, also results in costs associated with the resulting wastewater and the workup thereof, which make this process variant unattractive for industrial scale preparation.

In preparing triethyl phosphate, the workup is particularly difficult owing to the complete miscibility of ethanol and triethyl phosphate with water, since ethanol has to be distilled out of the aqueous phase and triethyl phosphate has to be extracted from the aqueous phase and then isolated. This results in undesirable losses of product, ethanol and extractant.

There is accordingly a need for an improved process for preparing triethyl phosphate which, with regard to process economy and ecology, meets at the same time the requirements for industrial scale preparation by:

a) removing the hydrogen chloride in such a manner that there is ideally no acidolysis of triethyl phosphate, no loss of ethanol and no additional cost due to the use or disposal of additional materials, such as bases or extractants, b) removing the heat of reaction in an efficient manner and c) keeping the ethanol excess as small as possible.

SUMMARY OF THE INVENTION

Surprisingly, there has now been found a process for preparing triethyl phosphate wherein a) phosphorus oxychloride is reacted with a greater than stoichiometric quantity of ethanol under reduced pressure at temperatures of from 0 to 50° C. in a reaction vessel, and the volatile components resulting from the reaction are predominantly condensed by means of a reflux condenser and the remaining volatile components are passed into a scrubber filled with water, b) after the end of the reaction, the reaction mixture is separated distillatively in a distillation column, referred to hereinbelow as an outgassing column, into a top product and a bottom product which predominantly comprises triethyl phosphate, c) the top product of the outgassing column is combined with the contents of the scrubber and d) the contents of the scrubber are subjected to a distillation, referred to hereinbelow as an azeotropic distillation, to obtain water and ethanol as top product and the ethanol, preferably after dewatering, is preferably returned to the reaction.

The process according to the invention enables the heat of reaction to be removed effectively and economically, since ethanol and hydrogen chloride boil under the conditions mentioned, so that volatile components arise in the form of a mixture of ethanol and hydrogen chloride, and the heat of reaction is quickly and effectively removed by evaporative cooling. The reflux from the reflux condenser also contributes advantageously to cooling of the reaction vessel.

The process according to the invention also enables the concentration of hydrogen chloride in the reaction mixture to be minimized. The loss of ethanol is likewise minimized by the process according to the invention. The portion of the gaseous ethanol which is not condensed by the reflux condenser and does not drop back into the reaction mixture is intercepted in the scrubber and recovered by distillative separation of the contents of the scrubber. The process according to the invention also enables the excess of ethanol which has to be used in the process to be reduced.

The process according to the invention can be implemented industrially in a simple and advantageous manner and further leads to triethyl phosphate in high yields and purities.

DETAILED DESCRIPTION OF THE INVENTION

The invention is described more fully hereunder with particular reference to its preferred embodiments. Preference is given to using the reactants phosphorus oxytrichloride and ethanol in the process according to the invention in technical grade purity. Particular preference is given to using highly pure products, since this enables the best yields to be achieved. Very particular preference is given to using ethanol having a very low water content, preferably from 0 to 0.3% by weight of water, more preferably from 0 to 0.1% by weight of water.

In the process according to the invention, a greater than stoichiometric quantity of ethanol is used, based on phosphorus oxytrichloride. Preference is given to using from 3 to 15 mol of ethanol per mole of phosphorus oxytrichloride, more preferably from 4 to 10 mol, and most preferably from 4.5 to 6.5 mol.

Step a) of the process according to the invention is carried out under reduced pressure, preferably at a pressure of from 30 to 600 mbar, more preferably at a pressure of from 60 to 250 mbar, and most preferably at a pressure of from 80 to 150 mbar.

Preference is given to operating the reflux condenser in the process according to the invention at temperatures of from −50 to 0° C., preferably from −40 to −5° C., and more preferably from −30- to −10° C.

The temperature in step a) of the process according to the invention is from 0 to 50° C., preferably from 5 to 50° C., and more preferably from 10 to 30° C.

The reaction vessel used in step a) of the process according to the invention is a customary reaction vessel known to those skilled in the art which is suitable for the reaction conditions mentioned. Preference is given to providing the reaction vessels with additional external cooling. Preference is also given to providing them with a stirring device. Preference is given to using a multistage reaction vessel, more preferably with a stirrer battery which consists of individual stirred vessels. In such multistage reaction vessels, preference is given to increasing the reaction temperature in each further reaction vessel in stages, in such a way that the temperature in the last reaction vessel is preferably from 25 to 35° C. This results in a commercially viable reaction time which is typically from about 6–8 h.

The volatile components arising in step a) in the process according to the invention contain predominantly of ethanol and hydrogen chloride.

A substantial portion of these volatile components condenses on the reflux condenser and contributes advantageously to the cooling of the reaction vessel by the reflux into the reaction mixture. The portion of the volatile constituents which is not condensed on the reflux condenser is passed into the water-filled scrubber. Preference is given to effecting this transfer via a butterfly valve, since this enables the desired pressure in the reaction vessel to be regulated.

After the end of step a) of the process according to the invention, preference is given to freeing the reaction mixture of volatile components in the outgassing column in step b) immediately after step a).

Preference is given to carrying out the distillation in the outgassing column in step b) at a pressure of from 10 to 100 mbar, more preferably from 15 to 60 mbar, and most preferably from 20 to 40 mbar, which results in a bottom temperature of from about 105 to 115° C. The bottom product obtained from the distillation contains predominantly triethyl phosphate, preferably of over 95% by weight of triethyl phosphate.

In a preferred form of the process according to the invention, the triethyl phosphate obtained is further purified by distillation. Preference is given to effecting this distillation at a pressure of from 2 to 50 mbar, more preferably from 5 to 20 mbar, and most preferably from 10 to 15 mbar. Triethyl phosphate which preferably has a purity of more than 99% by weight is obtained at the top at temperatures of from about 80 to 90° C. The bottom product obtained is predominantly diethyl phosphate.

Preference is given to condensing the top product obtained from the distillation in the outgassing column in step b) of the process according to the invention which contains predominantly of a mixture of ethanol and hydrogen chloride. Preference is given to carrying out the condensation at temperatures of from −40 to −10° C., and more preferably at from −25 to −17° C. This condensation step results in a top product which contains a condensate and of volatile components. The condensate is combined with the contents of the scrubber, preferably without intermediate storage. Preference is given to combining it with the contents of the scrubber by passing the condensate into the effluent of the scrubber. The combination of the condensate with the contents of the scrubber almost completely suppresses the undesired reaction of ethanol with hydrogen chloride to form ethyl chloride. The volatile components of the top product are likewise combined with the contents of the scrubber, and preference is given to passing them into the water-filled scrubber.

The scrubber used in the process according to the invention is filled with water. Preference is given to operating it at a temperature of from 5 to 20° C., and greater preference to operating it at from 7 to 15° C. The pressure in the scrubber is preferably from 10 to 100 mbar, and more preferably from 15 to 25 mbar.

The scrubber used in the process according to the invention preferably has a device for feeding in fresh water which is preferably located at the top of the scrubber. Preference is given to feeding in such a quantity of fresh water that the composition in the liquid phase of the scrubber, combined with the condensate of the top product from step b) of the process according to the invention gives a mixture which, as well as ethanol, also contains from 80 to 90 parts by weight of water, based on from 10 to 20 parts by weight of hydrogen chloride. Greater preference is given to adding such a quantity of fresh water that the distillative separation of the contents of the scrubber effected in step d) of the process according to the invention gives a top stream which has a composition very close to the azeotropic mixture of ethanol and water, and a bottom stream which has a composition very close to the azeotropic mixture of hydrogen chloride and water. The scrubber preferably has an outlet in its lower section, preferably in the form of a scrubbing circuit. In a preferred form, the outlet is attached to a distillation column which serves to distillatively separate the contents of the scrubber which are discharged via the outlet.

In step d) of the process according to the invention, the contents of the scrubber are separated distillatively in the azeotropic distillation into a top product which comprises predominantly ethanol and a small proportion of water, and a bottom product which comprises predominantly water and a small proportion of hydrogen chloride. The top product preferably comprises from 80 to 96% by weight of ethanol and from 4 to 20% by weight of water and the bottom product preferably comprises from 80 to 90% by weight of water and from 10 to 20% by weight of hydrogen chloride.

In a preferred embodiment, the azeotropic distillation in step d) is carried out at atmospheric pressure, and a top product which comprises about 90% by weight of ethanol is withdrawn at the top at about 75° C. and the bottom stream boils at about 110° C. and comprises about 18% by weight of hydrogen chloride.

The aqueous ethanol obtained as top product can be dewatered by methods known to those skilled in the art. Preference is given to carrying out the dewatering using glycol. In a preferred embodiment of the process according to the invention, the dewatered ethanol is returned back into the reaction a).

In a preferred embodiment, the process according to the invention is carried out in whole or in part by a continuous method. The reaction vessels used in the continuous method are preferably tube reactors, reaction loops, reaction columns or reaction batteries.

The following non-limiting examples illustrate the process according to the invention.

EXAMPLES

Example 1

The reaction was carried out in a stirred tank battery consisting of three stirred tanks each having a liquid capacity of 1 liter. The three stirred tanks were connected to each other and to a reservoir via a submerged connection so that the reaction product was free to overflow into the reservoir. All three stirred tanks were equipped with reflux condensers which were connected to each other and to a cooling circuit at −20° C.

The first stirred tank was kept by means of external cooling (thermostat) at an internal temperature (reaction temperature) of from 3 to 6° C., the second stirred tank at from 13 to 15° C. and the third stirred tank at from 18 to 20° C. 517.5 g/h of ethanol (11.25 mol/h) and 383.8 g/h of phosphorus oxytrichloride (2.5 mol/h) was continuously metered into the first stirred tank.

The stirred tank battery and the reservoir were connected via a valve and via a scrubber to a vacuum pump which was used to hold the pressure in the stirred tank battery at 50 mbar. The internal pressure of the first stirred tank was set to 100 mbar with the aid of a further valve. The reflux condensers condensed a mixture of hydrogen chloride and ethanol which predominantly flowed back into the stirred tanks. The remaining volatile components were passed into the scrubber.

The scrubber consisted of a randomly packed column into which 1270 g/h of fresh water were fed from above and the lower portion was operated using a scrubbing circuit at a temperature of 8° C. The pressure in the scrubber was set to 20 mbar. From the scrubbing circuit, 1712 g/h of liquid were fed constantly into a distillation column attached to it for azeotropic distillation. At the top of this distillation column, about 190 g/h of a mixture of 90% by weight of ethanol and 10% by weight of water were withdrawn at a temperature of 74° C. and a pressure of 1013 mbar. At the bottom of this distillation column, about 1520 g/h of a mixture of 82% by weight of water and 18% by weight of hydrogen chloride were removed at 109° C. and a pressure of 1013 mbar.

The mixture of 90% by weight of ethanol and 10% by weight of water was admixed with 530 g/h of glycol and water-free ethanol was removed as the top product in a further distillation and returned to the reaction with phosphorus oxytrichloride. On average, the loss of ethanol was about 2.3% by weight, based on the quantity added to the reaction.

On attainment of equilibrium in the stirred tank battery, the reaction product obtained in the reservoir consisted of 75.9% by weight of triethyl phosphate, 20.1% by weight of ethanol and 4% by weight of hydrogen chloride. It was separated in an outgassing column without further storage. The outgassing column was operated at a pressure of from 30 to 34 mbar which resulted in a temperature of 14° C. at the top and 112° C. at the bottom. The top of the column was equipped with a condenser which was operated using a cooling circuit at −20° C. The condensate was passed directly to the scrubbing circuit of the scrubber and all non-condensable, volatile components were passed into the scrubber from below. At the bottom of the outgassing column, 457 g/h of a crude product were removed which consisted of 96.3% by weight of triethyl phosphate.

The crude product was then subjected to purification by distillation. At a top temperature of 84° C. at 10 mbar and a bottom temperature of 141° C. at 16 mbar, 435 g/h of triethyl phosphate in a purity of greater than 99% by weight were obtained. This corresponds to a yield of 95.6%, based on phosphorus oxytrichloride used. At the bottom of the column, 20 g/h of a mixture were removed which consisted of 67% by weight of diethyl phosphate.

Example 2

Example 2 was carried out in a similar manner to example 1, except that 598 g/h of ethanol (13 mol/h) and 307 g/h of phosphorus oxytrichloride (2 mol/h) were continuously metered into the first stirred tank.

On attainment of equilibrium in the stirred tank battery, the reaction product obtained in the reservoir consisted of 57.4% by weight of triethyl phosphate, 35.5% by weight of ethanol and 7.1% by weight of hydrogen chloride. Separation in the outgassing column gave 367 g/h of a crude product which consisted of 96.8% by weight of triethyl phosphate. The product obtained after purification by distillation contained over 99% by weight of triethyl phosphate, and the yield was 96.3%, based on phosphorus oxychloride used.

1034 g/h of fresh water were fed into the scrubber from above and about 1575 g/h of liquid from the scrubbing circuit were fed into a connected distillation column for azeotropic distillation. At the top of this distillation column, 358 g/h of a mixture of 90% by weight of ethanol and 10% by weight of water were withdrawn. At the bottom of this distillation column, 1217 g/h of a mixture of 82% by weight of water and 18% by weight of hydrogen chloride were removed.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for preparing triethyl phosphate comprising reacting phosphorus oxychloride with a greater than stoichiometric quantity of ethanol under reduced pressure at temperatures of from 0 to 50° C. in a reaction vessel, wherein
   a) volatile components resulting from the reaction are predominantly condensed by means of a reflux condenser and the remaining volatile components are passed into a scrubber filled with water,
   b) after the end of the reaction, the resulting reaction mixture is separated distillatively in an outgassing column into a top product and a bottom product which predominantly comprises triethyl phosphate,
   c) the top product of the outgassing column is combined with the contents of the scrubber and
   d) the contents of the scrubber are separated distillatively in an azeotropic distillation to obtain water and ethanol as top product and the ethanol after dewatering, is returned to the reaction.

2. Process according to claim 1, wherein from 3 to 15 mol of ethanol per mole of phosphorus oxychloride are used.

3. Process according to claim 1 wherein the reaction is carried out at a pressure of from 30 to 600 mbar.

4. Process according to claim 1 wherein the reflux condenser is operated at a temperature of from −50 to 0° C.

5. Process according to claim 1 wherein the distillation in the outgassing column in step b) is carried out at a pressure of from 10 to 100 mbar.

6. Process according to claim 1 wherein the bottom product from the outgassing column in step b) contains over 95% by weight of triethyl phosphate.

7. Process according to claim 1 wherein the top product from the outgassing column in step b) contains volatile components which are passed into the scrubber and a condensate which is added with the effluent of the scrubber.

8. Process according to claim 1 wherein the contents of the scrubber in step d) contain predominantly water, ethanol and hydrogen chloride.

9. Process according to claim 1 wherein the water quantity in the scrubber is determined in such a way that, based on from 10 to 20 parts by weight of hydrogen chloride, there are from 80 to 90 parts by weight of water.

10. Process according to claim 1 wherein the contents of the scrubber are passed through an outlet into a distillation column for azeotropic distillation and are distillatively separated there into a top product which comprises predominantly ethanol and a small proportion of water, and a bottom product which comprises predominantly water and a small proportion of hydrogen chloride.

11. Process according to claim 1 wherein the contents of the scrubber are passed via an outlet into a distillation column for azeotropic distillation and are separated there into a top product which comprises from 80 to 96% by weight of ethanol and from 4 to 20% by weight of water, and a bottom product which comprises from 80 to 90% by weight of water and from 10 to 20% by weight of hydrogen chloride.

12. Process according to claim 1 wherein the top product from the azeotropic distillation in step d) is dewatered and the ethanol obtained is returned to the reaction.

13. Process according to claim 1 wherein the bottom product from the outgassing column in step b) is purified in a further distillation.

14. Process according to claim 1 wherein the bottom product from the outgassing column in step b) is purified in a further distillation which is carried out at a pressure of from 2 to 50 mbar.

15. Process according to claim 1 wherein the process is operated in whole or in part in a continuous method.

* * * * *